United States Patent
Zeiller et al.

(10) Patent No.: US 7,465,752 B2
(45) Date of Patent: Dec. 16, 2008

(54) PENTENOIC ACID DERIVATIVES, PROCESSES FOR THE PREPARATION THEREOF, PHARMACEUTICAL COMPOSITIONS COMPRISING THEM, AND THERAPEUTIC APPLICATIONS THEREOF

(75) Inventors: Jean Jacques Zeiller, Lyons (FR); Hervè Dumas, Vaulx Milieu (FR); Valérie Guyard-Dangremont, Saint Maurice de Gourdans (FR); Isabelle Berard, Villard les Dombes (FR); Francis Contard, Lyons (FR); Daniel Guerrier, Saint Genis Laval (FR); Gérard Ferrand, Lyons (FR); Yves Bonhomme, Charbonnières les Bains (FR)

(73) Assignee: Merck Patent GmbH, Darmstadt (DE)

( * ) Notice: Subject to any disclaimer, the term of this patent is extended or adjusted under 35 U.S.C. 154(b) by 84 days.

(21) Appl. No.: 11/568,598

(22) PCT Filed: Apr. 6, 2005

(86) PCT No.: PCT/EP2005/003605

§ 371 (c)(1),
(2), (4) Date: Nov. 2, 2006

(87) PCT Pub. No.: WO2005/105723

PCT Pub. Date: Nov. 10, 2005

(65) Prior Publication Data

US 2008/0015253 A1    Jan. 17, 2008

(30) Foreign Application Priority Data

May 3, 2004   (FR) .................................. 04 04712

(51) Int. Cl.
| | | |
|---|---|---|
| *A61K 31/38* | (2006.01) | |
| *A61K 31/235* | (2006.01) | |
| *A61K 31/19* | (2006.01) | |
| *C07D 227/04* | (2006.01) | |
| *C07C 69/76* | (2006.01) | |
| *C07C 59/54* | (2006.01) | |

(52) U.S. Cl. ........................ 514/443; 514/543; 514/571; 548/146; 560/62; 562/472

(58) Field of Classification Search ................. None
See application file for complete search history.

(56) References Cited

FOREIGN PATENT DOCUMENTS

| DE | 35 12 820 A1 | 10/1986 |
|---|---|---|
| FR | 2 682 677 A | 4/1993 |
| JP | 52 072819 A | 6/1977 |

OTHER PUBLICATIONS

Rudler et al, Journal of Organometallic Chemistry, Transition-metal Catalyzed Synthesis of delta-Hydroxy-gamma-Lactones from Bis (Trimethylsily) Ketene Acetals and Allylic Acetates Via gamma-Unsaturated Carboxylic Acids. Comments on the Formation of alpha-Cyclopropyl Carboxylic Acids, 2001, 624, pp. 186-202.*
International Search Report issued in PCT/EP2005/003605 dated Apr. 6, 2005.
K. Mikami et al., "Catalytic Asymmertic Glyoxylate-Ene Reaction: A practical access to Alpha-hydroxy esters in high enantiomeric purities", Journal of the Amer. Chem. Soc., vol. 112, No. 10, (1990) pp. 3949-3954.
Ando et al., "Reaction of Carbethoxycarbene with Aliphatic Sulfides and Allyl Compounds", J. Org. Chem., vol. 36, No. 13, (1971) pp. 1732-1736.

* cited by examiner

*Primary Examiner*—Paul A Zucker
(74) *Attorney, Agent, or Firm*—Millen, White, Zelano, Branigan

(57) ABSTRACT

Compounds of the formula (I):

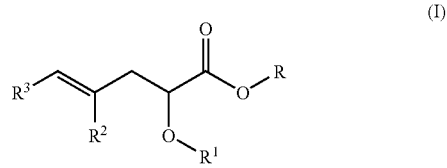

in which R, $R^1$, $R^2$ and $R^3$ are as defined in the description, to their use for the treatment of dyslipidaemia, atherosclerosis and diabetes, to pharmaceutical compositions comprising them and to the processes for the preparation of these compounds.

14 Claims, No Drawings

PENTENOIC ACID DERIVATIVES, PROCESSES FOR THE PREPARATION THEREOF, PHARMACEUTICAL COMPOSITIONS COMPRISING THEM, AND THERAPEUTIC APPLICATIONS THEREOF

The present invention relates to unsaturated carboxylic acid derivatives that can be used in the treatment of dyslipidaemia, atherosclerosis and diabetes, to pharmaceutical compositions comprising them, and to processes for the preparation of these compounds.

The invention also relates to the use of these compounds for the preparation of medicaments for the treatment of dyslipidaemia, atherosclerosis and diabetes.

In most countries, cardiovascular disease remains one of the major diseases and the main cause of death. About one third of men develop a major cardiovascular disease before the age of 60, with women showing a lower risk (ratio of 1 to 10). With advancing years (after the age of 65, women become just as vulnerable to cardiovascular diseases as men), this disease increases even more in scale. Vascular diseases, such as coronary disease, strokes, restenosis and peripheral vascular disease remain the prime cause of death and handicap world-wide.

Whereas the diet and lifestyle can accelerate the development of cardiovascular diseases, a genetic predisposition leading to dyslipidaemia is a significant factor in cardiovascular accidents and death.

The development of atherosclerosis appears to be linked mainly to dyslipidaemia, which means abnormal levels of lipoproteins in the blood plasma. This dysfunction is particularly evident in coronary disease, diabetes and obesity.

The concept intended to explain the development of atherosclerosis was mainly focused on the metabolism of cholesterol and on the metabolism of triglycerides.

However, since the studies of Randle et al. (Lancet, 1963, 785-789), a novel concept has been proposed: a glucose-fatty acid cycle or Randle cycle, which describes the regulation of the equilibrium between the metabolism of lipids in terms of triglycerides and cholesterol, and the oxygenation of glucose. Following this concept, the inventors have developed a novel programme, the aim of which is to find novel compounds acting simultaneously on lipid metabolism and glucose metabolism.

Fibrates are well-known therapeutic agents with a mechanism of action via the "Peroxisome Proliferator Activated Receptors". These receptors are the main regulators of lipid metabolism in the liver (PPARα isoform). In the last 10 years, thiazolidinediones have been described as powerful hypoglycaemiant agents in man and animals. It has been reported that thiazolidinediones are powerful selective activators of another isoform of PPARs: PPARγ (Lehmann et al., J. Biol. Chem., (1995), 270, 12953-12956).

The inventors have discovered a novel class of compounds that are powerful activators of the PPARα and PPARγ isoforms. As a result of this activity, these compounds have a substantial hypolipidaemiant and hypoglycaemiant effect.

More specifically, the invention relates to compounds derived from pentenoic acid, of the formula (I):

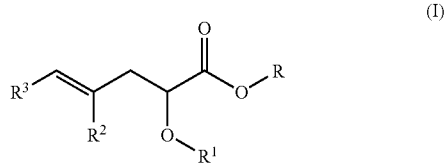

in which:
$R^1$ represents a $(C_6-C_{18})$aryl radical substituted by and/or fused to a saturated or unsaturated 5- to 8-membered monocyclic or polycyclic nucleus optionally containing one or more hetero atoms chosen from O, N and S, the said nucleus itself being optionally substituted;
$R^2$ and $R^3$, which may be identical or different, are chosen, independently of each other, from a hydrogen atom and a $(C_6-C_{18})$aryl radical; and
R is chosen from a hydrogen atom and a $C_1-C_{10}$ alkyl radical;
the geometrical and optical isomers thereof, and also the pharmaceutically acceptable addition salts thereof with acids or bases,
it being understood that the compound in which $R^2$=H, $R^3$=H, R=H or ethyl and $R^1$=(2-chloro-4-trifluoromethyl) phenoxyphenyl is excluded from protection.

The compound indicated above and excluded from the subject of the present invention is disclosed as an insecticide in patent application JP 52072819. Other pentenoic acid derivatives have also been disclosed, especially by A. Mittra et al. (J. Org. Chem., (1993), 58(27), 7913-15). The said document describes a process for synthesizing benzodioxabicyclo[3.3.0]-octanes.

The acids that can be used to form the salts of the compounds of the formula (I) are mineral or organic acids. The resulting salts are, for example, the hydrochlorides, hydrobromides, sulfates, hydrogen sulfates, dihydrogen phosphates, citrates, maleates, fumarates, 2-naphthalenesulfonates and para-toluenesulfonates.

The bases that can be used to form the salts of the compounds of the formula (I) are mineral or organic bases. The resulting salts are, for example, the salts formed with metals and especially alkali metals, alkaline-earth metals and transition metals (such as sodium, potassium, calcium, magnesium or aluminium), or with bases, for instance ammonia or secondary or tertiary amines (such as diethylamine, triethylamine, piperidine, piperazine or morpholine) or with basic amino acids, or with osamines (such as meglumine) or with amino alcohols (such as 3-aminobutanol and 2-aminoethanol).

The invention especially covers the pharmaceutically acceptable salts, but also the salts that allow a suitable separation or crystallization of the compounds of the formula (I), such as the salts obtained with chiral amines.

The invention also covers the stereoisomers of the compounds of the formula (I), and also mixtures of stereoisomers in all proportions.

The compounds of the formula (I) above also comprise the prodrugs of these compounds.

The term "prodrugs" means compounds which, once administered to the patient, are chemically and/or biologically converted by the live organism into compounds of the formula (I).

According to the invention, the term "aryl radical" means a monocyclic or polycyclic carbocyclic aromatic group preferably containing from 6 to 18 carbon atoms. Aryl radicals that may be mentioned include phenyl, naphthyl, anthryl and phenanthryl groups.

The term "alkyl" means a linear or branched hydrocarbon-based chain containing from 1 to 10 carbon atoms and better still from 1 to 6 carbon atoms, for example from 1 to 4 carbon atoms.

Examples of alkyl radicals are methyl, ethyl, propyl, isopropyl, butyl, iso-butyl, t-butyl, pentyl, isopentyl, neopentyl, 2-methylbutyl, 1-ethylpropyl, hexyl, iso-hexyl, neohexyl, 1-methylpentyl, 3-methylpentyl, 1,1-dimethylbutyl, 1,3-dimethylbutyl, 1-ethylbutyl, 1-methyl-1-ethylpropyl, heptyl, 1-methylhexyl, 1-propylbutyl, 4,4-dimethylpentyl, octyl, 1-methylheptyl, 2-methylhexyl, 5,5-dimethylhexyl, nonyl, decyl, 1-methylnonyl, 3,7-dimethyloctyl and 7,7-dimethyloctyl.

The heterocyclic radicals are monocyclic or polycyclic radicals comprising one or more hetero atoms generally chosen from O, S and N, optionally in oxidized form (in the case of S and N).

Preferably, at least one of the monocycles constituting the heterocycle comprises from 1 to 4 endocyclic hetero atoms and better still from 1 to 3 hetero atoms.

According to the invention, the polycyclic heterocyclic nucleus consists of one or more monocycles, each of which is 5- to 8-membered.

Examples of 5- to 8-membered monocyclic aromatic heterocyclic radicals are heteroaryl radicals derived from heteroaromatic compounds, such as pyridine, furan, thiophene, pyrrole, imidazole, thiazole, isoxazole, isothiazole, furazane, pyridazine, pyrimidine, pyrazine, thiazines, oxazole, pyrazole, oxadiazole, triazole and thiadiazole.

Preferred heteroaryl radicals that may be mentioned include pyridyl, pyrimidinyl, triazolyl, thiadiazolyl, oxazolyl, thiazolyl and thienyl radicals.

The saturated or unsaturated heterocyclic groups are heterocyclic groups bearing no unsaturation, or comprising one or more unsaturations derived from the aromatic heterocyclic groups defined above, respectively.

Unless otherwise mentioned, the aryl and heterocyclic radicals may be optionally substituted by one or more of the following radicals G, which may be identical or different:

trifluoromethyl; a halogen atom; a monocyclic, bicyclic or tricyclic aromatic heterocyclic radical comprising one or more hetero atoms chosen from O, N and S; and optionally substituted by one or more radicals T as defined below; a group Het-CO—, in which Het represents an aromatic heterocyclic radical as defined above optionally substituted by one or more radicals T; a $C_1$-C6 alkylenediyl chain; a $C_1$-$C_6$ alkylenedioxy chain; nitro; cyano; ($C_1$-$C_{10}$)alkyl; ($C_1$-$C_{10}$)alkylcarbonyl; ($C_1$-$C_{10}$)alkoxycarbonyl-A-, in which A represents ($C_1$-$C_6$)alkylene, ($C_2$-$C_6$)-alkenylene or a bond; ($C_3$-$C_{10}$)cycloalkyl; trifluoromethoxy; di($C_1$-$C_{10}$)alkylamino; ($C_1$-$C_{10}$)alkoxy($C_1$-$C_{10}$)alkyl; ($C_1$-$C_{10}$)alkoxy; ($C_6$-$C_{18}$)aryl optionally substituted by one or more radicals T; ($C_6$-$C_{18}$)aryl ($C_1$-$C_{10}$)alkoxy-(CO)$_n$—, in which n is 0 or 1 and aryl is optionally substituted by one or more radicals T; ($C_6$-$C_{18}$) aryloxy(CO)$_n$—, in which n is 0 or 1 and in which aryl is optionally substituted by one or more radicals T; ($C_6$-$C_{18}$) arylthio, in which aryl is optionally substituted by one or more radicals T; ($C_6$-$C_{18}$)aryloxy($C_1$-$C_{10}$)alkyl(CO)$_n$—, in which n is 0 or 1 and in which aryl is optionally substituted by one or more radicals T; a saturated or unsaturated, monocyclic 5- to 8-membered heterocycle comprising one or more hetero atoms chosen from O, N and S, optionally substituted by one or more radicals T; ($C_6$-$C_{18}$)arylcarbonyl optionally substituted by one or more radicals T; ($C_6$-$C_{18}$)arylcarbonyl-B—(CO)$_n$—, in which n is 0 or 1; B represents ($C_1$-$C_6$)alkylene or ($C_2$-$C_6$)alkenylene and aryl is optionally substituted by one or more radicals T; ($C_6$-$C_{18}$)aryl-C—(CO)$_n$—, in which n is 0 or 1, C represents ($C_1$-$C_6$)alkylene or ($C_2$-$C_6$)alkenylene and aryl is optionally substituted by one or more radicals T; ($C_6$-$C_{18}$)aryl fused to a saturated or unsaturated heterocycle as defined above, optionally substituted by one or more radicals T; ($C_2$-$C_{10}$)alkynyl; T is chosen from a halogen atom; ($C_6$-$C_{18}$)aryl; ($C_1$-$C_6$)alkyl; ($C_1$-$C_6$)alkoxy; nitro; carboxyl; ($C_1$-$C_6$)alkoxycarboxyl; and T may represent oxo in the case where it substitutes a saturated or unsaturated heterocycle; or T represents ($C_1$-$C_6$)alkoxycarbonyl($C_1$-$C_6$)alkyl; or ($C_1$-$C_6$) alkylcarbonyl(($C_1$-$C_6$)-alkyl)$_n$—, in which n is 0 or 1.

T preferably represents a halogen atom or a ($C_1$-$C_6$)alkyl radical.

The term "halogen atom" means a chlorine, bromine, iodine or fluorine atom.

The monocyclic, bicyclic or tricyclic aromatic heterocyclic radicals preferably comprise one or more hetero atoms generally chosen from O, S and N, optionally in oxidized form (in the case of S and N). Preferably, at least one of the monocycles constituting the heterocycle comprises from 1 to 4 endocyclic hetero atoms and better still from 1 to 3 hetero atoms.

Preferably, the heterocycle consists of one or more monocycles, each of which is 5- to 8-membered.

Examples of 5- to 8-membered monocyclic heteroaryls are especially pyridine, furan, thiophene, pyrrole, imidazole, thiazole, isoxazole, isothiazole, furazane, pyridazine, pyrimidine, pyrazine, thiazines, oxazole, pyrazole, oxadiazole, triazole and thiadiazole.

Examples of bicyclic heteroaryls in which each monocycles is 5- to 8-membered are chosen from indolizine, indole, isoindole, benzofuran, benzothiophene, indazole, benzimidazole, benzothiazole, benzofurazane, benzothiofurazane, purine, quinoline, isoquinoline, cinnoline, phthalazine, quinazoline, quinoxaline, naphthyridine, pyrazolotriazine (such as pyrazolo-1,3,4-triazine), pyrazolopyrimidine and pteridine.

Preferred heteroaryl radicals that may be mentioned include quinolyl, pyridyl, benzothiazolyl and triazolyl radicals.

The tricyclic heteroaryls in which each monocycle is 5- to 8-membered are chosen, for example, from acridine, phenazine and carbazole.

The term "alkylenediyl chain" means a divalent radical of linear or branched aliphatic hydrocarbon-based type derived from the alkyl groups defined above by stripping out a hydrogen atom. Preferred examples of alkylenediyl chains are chains —(CH$_2$)$_k$—, in which k represents an integer chosen from 2, 3, 4, 5 and 6 and C(CH$_3$)$_2$ and —CH$_2$—C(CH$_3$)$_2$—CH$_2$— chains. The alkylenedioxy chains denote —O-Alk-O— chains, in which Alk represents linear or branched alkylene, it being understood that alkylene is as defined above for alkylenediyl. Preferred meanings of —O-Alk-O— are, for example, —O—C(CH$_3$)$_2$—O or —O—CH$_2$—CH$_2$—O—.

The term "alkenylene" defines an unsaturated alkylene chain containing one or more ethylenic unsaturations, preferably one to three ethylenic unsaturations. Examples of alkenylene chains are —CH=CH— or —CH=CH—CH=CH—.

Examples of $C_3$-$C_{10}$ cycloalkyl groups are especially cyclopropyl, cyclobutyl, cyclopentyl, cyclohexyl, cycloheptyl, cyclooctyl or cyclodecyl groups.

Saturated or unsaturated, monocyclic 5- to 8-membered heterocycles are saturated, or unsaturated, derivatives of aromatic heterocycles.

Mention may be made more particularly of morpholine, piperidine, thiazolidine, oxazolidine, tetrahydrothienyl, tetrahydrofuryl, pyrrolidine, isoxazolidine, imidazolidine or pyrazolidine.

The term "alkynyl" means an aliphatic hydrocarbon-based group containing one or more unsaturations of acetylenic type. A preferred example is —C≡C—.

A preferred group of compounds of the invention consists of compounds for which $R^1$ represents substituted ($C_6$-$C_{10}$) aryl;

$R^2$ and $R^3$, which may be identical or different, are chosen, independently of each other, from a hydrogen atom and a ($C_6$-$C_{10}$)aryl radical; and R is chosen from a hydrogen atom and a $C_1$-$C_{10}$ alkyl radical.

Another preferred group of compounds of the invention consists of compounds for which $R^3$ represents a hydrogen atom or an optionally substituted ($C_6$-$C_{10}$)aryl radical and $R^2$ is a hydrogen atom, the other substituents being as defined in the general formula (I) or in the preceding preferred group.

Another even more preferred group of compounds of the invention consists of compounds for which $R^3$ represents an optionally substituted phenyl, preferably unsubstituted phenyl, the other substituents being as defined in the general formula (I) or in the preferred groups defined above.

Another preferred group of compounds of the invention consists of compounds for which $R^1$ represents ($C_6$-$C_{18}$)aryl substituted by one or more optionally halogenated alkyl radicals, the other substituents being as defined in the general formula (I) or in the preferred groups defined above.

Another preferred group of compounds of the invention consists of compounds for which R represents a hydrogen atom or a ($C_1$-$C_{10}$)alkyl radical, the other substituents being as defined in the general formula (I) or in the preferred groups defined above.

Another even more preferred group of compounds of the invention consists of compounds for which $R^1$ represents a substituted $C_6$-$C_{10}$ aryl radical, $R^2$ being H, $R^3$ being unsubstituted aryl and R being H.

Another even more preferred group of compounds of the invention consists of compounds for which $R^1$ represents a substituted $C_6$-$C_{10}$ aryl radical, $R^2$ being H, $R^3$ being unsubstituted aryl and R being alkyl.

When $R^1$ represents a substituted ($C_6$-$C_{18}$)aryl radical, the aryl nucleus is preferably substituted by one or more of the following radicals:

trifluoromethyl; a halogen atom; a monocyclic, bicyclic or tricyclic aromatic heterocyclic radical comprising one or more hetero atoms chosen from O, N and S; and optionally substituted by one or more radicals T as defined below; a radical Het-CO—, in which Het represents an aromatic heterocyclic radical as defined above, optionally substituted by one or more radicals T; a $C_1$-$C_6$ alkylenediyl chain; a $C_1$-$C_6$ alkylenedioxy chain; nitro; cyano; ($C_1$-$C_{10}$)alkyl; ($C_1$-$C_{10}$)alkylcarbonyl; ($C_1$-$C_{10}$)alkoxycarbonyl-A-, in which A represents ($C_1$-$C_6$)alkylene, ($C_2$-$C_6$)-alkenylene or a bond; ($C_3$-$C_{10}$)cycloalkyl; trifluoromethoxy; di($C_1$-$C_{10}$)alkylamino; ($C_1$-$C_{10}$)alkoxy($C_1$-$C_{10}$)alkyl; ($C_1$-$C_{10}$)alkoxy; ($C_6$-$C_{18}$)aryl optionally substituted by one or more radicals T; ($C_6$-$C_{18}$)aryl ($C_1$-$C_{10}$)alkoxy-(CO)$_n$—, in which n is 0 or 1 and aryl is optionally substituted by one or more radicals T; ($C_6$-$C_{18}$) aryloxy(CO)$_n$—, in which n is 0 or 1 and in which aryl is optionally substituted by one or more radicals T; ($C_6$-$C_{18}$) arylthio, in which aryl is optionally substituted by one or more radicals T; ($C_6$-$C_{18}$)aryloxy($C_1$-$C_{10}$)alkyl(CO)$_n$—, in which n is 0 or 1 and in which aryl is optionally substituted by one or more radicals T; a saturated or unsaturated, monocyclic 5- to 8-membered heterocycle comprising one or more hetero atoms chosen from O, N and S, optionally substituted by one or more radicals T; ($C_6$-$C_{18}$)arylcarbonyl optionally substituted by one or more radicals T; ($C_6$-$C_{18}$)arylcarbonyl-B-(CO)$_n$—, in which n is 0 or 1; B represents ($C_1$-$C_6$)alkylene or ($C_2$-$C_6$)alkenylene and aryl is optionally substituted by one or more radicals T; ($C_6$-$C_{18}$)aryl-C—(CO)$_n$—, in which n is 0 or 1, C represents ($C_1$-$C_6$)alkylene or ($C_2$-$C_6$)alkenylene and aryl is optionally substituted by one or more radicals T; ($C_6$-$C_{18}$)aryl fused to a saturated or unsaturated heterocycle as defined above, optionally substituted by one or more radicals T; ($C_2$-$C_{10}$)alkynyl; T is chosen from a halogen atom; ($C_6$-$C_{18}$)aryl; ($C_1$-$C_6$)alkyl; ($C_1$-$C_6$)alkoxy; nitro; carboxyl; ($C_1$-$C_6$)alkoxycarboxyl; and T may represent oxo in the case where it substitutes a saturated or unsaturated heterocycle; or alternatively T represents ($C_1$-$C_6$)alkoxycarbonyl($C_1$-$C_6$) alkyl; or ($C_1$-$C_6$)alkylcarbonyl(($C_1$-$C_6$)-alkyl)$_n$—, in which n is 0 or 1.

The compounds of the general formula (I) in which $R^2$ represents a hydrogen atom, the other substituents being as defined above, are also preferred.

The compounds of the formula (I) in which $R^3$ is chosen from a hydrogen atom and an unsubstituted ($C_6$-$C_{10}$)aryl group, especially unsubstituted phenyl, the other substituents being as defined above, are also preferred.

More particularly, the preferred compounds are those chosen from:

ethyl (R,S)-2-(4-trifluoromethylphenyl)oxypent-4-enoate;
(R,S)-2-(4-trifluoromethylphenyl)oxypent-4-enoic acid;
(R,S)-2-{[4-(5-chlorothien-2-yl)phenyl)oxy}-5-phenylpent-4-enoic acid;
(R,S)-2-[(4-bromophenyl)oxy]-5-phenylpent-4-enoic acid;
(R,S)-2-{[(4-benzo[b]thiophen-2-yl)phenyl]oxy}-5-phenylpent-4-enoic acid; and
(R,S)-2-{[4-(2-methyl-1,3-thiazol-4-yl)phenyl]oxy}-5-phenylpent-4-enoic acid.

The invention also relates to pharmaceutical compositions comprising a pharmaceutically effective amount of at least one compound chosen from a compound of the formula (I) as defined above in combination with one or more pharmaceutically acceptable vehicles.

These compositions can be administered orally in the form of tablets, gel capsules or granules with immediate release or controlled release, intravenously in the form of an injectable solution, transdermally in the form of an adhesive transdermal device, or locally in the form of a solution, cream or gel.

A solid composition for oral administration is prepared by adding to the active principle a filler and, where appropriate, a binder, a disintegrating agent, a lubricant, a colorant or a flavour enhancer, and by forming the mixture into a tablet, a coated tablet, a granule, a powder or a capsule.

Examples of fillers include lactose, corn starch, sucrose, glucose, sorbitol, crystalline cellulose and silicon dioxide, and examples of binders include poly(vinyl alcohol), poly (vinyl ether), ethylcellulose, methylcellulose, acacia, gum tragacanth, gelatine, shellac, hydroxypropylcellulose, hydroxypropylmethylcellulose, calcium citrate, dextrin and pectin. Examples of lubricants include magnesium stearate, talc, polyethylene glycol, silica and hardened plant oils. The colorant can be any of those permitted for used in medicaments. Examples of flavour enhancers include cocoa powder, mint in herb form, aromatic powder, mint in oil form, borneol and cinnamon powder. Obviously, the tablet or granule can be suitably coated with sugar, gelatin or the like.

An injectable form comprising the compound of the present invention as active principle is prepared, where appropriate, by mixing the said compound with a pH regulator, a buffer agent, a suspension agent, a solubilizer, a stabilizer, an isotonic agent and/or a preserving agent, and by converting the mixture into a form for intravenous, subcutaneous or intramuscular injection, according to a standard process. Where appropriate, the injectable form obtained can be freeze-dried via a standard process.

Examples of suspension agents include methylcellulose, polysorbate 80, hydroxyethylcellulose, acacia, powdered gum tragacanth, sodium carboxymethylcellulose and polyethoxylated sorbitan monolaurate.

Examples of solubilizers include castor oil solidified with polyoxyethylene, polysorbate 80, nicotinamide, polyethoxylated sorbitan monolaurate and the ethyl ester of castor oil fatty acid.

In addition, the stabilizer encompasses sodium sulfite, sodium metasulfite and ether, while the preserving agent encompasses methyl p-hydroxybenzoate, ethyl p-hydroxybenzoate, sorbic acid, phenol, cresol and chlorocresol.

The present invention also relates to the use of a compound of the formula (I) of the invention for the preparation of a medicament for the prevention of or treating dyslipidaemia, atherosclerosis and diabetes.

The effective administration doses and posologies of the compounds of the invention, intended for the prevention or treatment of a disease, disorder or condition caused by or associated with modulation of PPAR activity, depends on a large number of factors, for example on the nature of the inhibitor, the size of the patient, the aim of the desired treatment, the nature of the pathology to be treated, the specific pharmaceutical composition used and the observations and the conclusions of the treating physician.

For example, in the case of an oral administration, for example a tablet or a gel capsule, a possible suitable dosage of the compounds of the formula (I) is between about 0.1 mg/kg and about 100 mg/kg of body weight per day, preferably between about 0.5 mg/kg and about 50 mg/kg of body weight per day, more preferably between about 1 mg/kg and about 10 mg/kg of body weight per day and more preferably between about 2 mg/kg and about 5 mg/kg of body weight per day of active material.

If representative of body weights of 10 kg and 100 kg are considered in order to illustrate the oral daily dosage range that can be used and as described above, suitable dosages of the compounds of the formula (I) will be between about 1-10 mg and 1000-10 000 mg per day, preferably between about 5-50 mg and 500-5000 mg per day, more preferably between about 10.0-100.0 mg and 100.0-1000.0 mg per day and even more preferably between about 20.0-200.0 mg arid about 50.0-500.0 mg per day of active material comprising a preferred compound.

These dosage ranges represent total amounts of active material per day for a given patient. The number of administrations per day at which a dose is administered can vary within wide proportions depending on pharmacokinetic and pharmacological factors, such as the half-life of the active material, which reflects its rate of catabolism and clearance, and also the minimum and optimum levels of the said active material, in blood plasma or in other bodily fluids, which are reached in the patient and which are required for therapeutic efficacy.

Many other factors should also be taken into consideration when determining the number of daily administrations and the amount of active material that should be administered in a single dosage intake. Among these other factors, and not the least of which, is the individual response of the patient to be treated.

The compounds of the present invention can be prepared from compounds of the formula (III) according to the following reaction scheme:

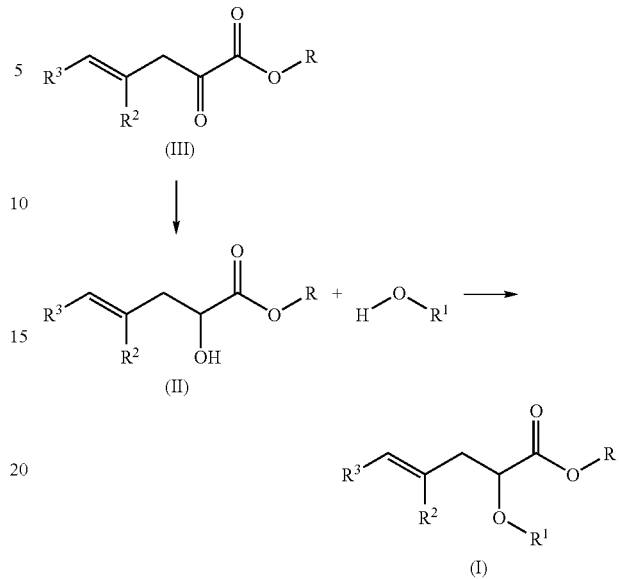

in which reaction scheme $R^1$, $R^2$, $R^3$ and R are as defined above for formula (I).

This reaction is preferably performed in an aromatic solvent or in a polar aprotic solvent, such as a linear or cyclic ether, for example diethyl ether, di-tertbutyl ether, diisopropyl ether or dimethoxyethane, or alternatively, such as dioxane or tetrahydrofuran, toluene and dimethoxyethane being preferred.

According to one preferred embodiment of the invention, the molar ratio of the compound of the formula (II) to the alcohol $R^1$—OH ranges between 1 and 1.5, an approximately stoichiometric ratio of between 1 and 1.3 and preferably between 1 and 1.15 being desirable.

In order to facilitate the reaction, it is desirable to add to the medium a coupling agent, such as a lower alkyl (i.e. $C_1$-$C_6$ alkyl) azodicarboxylate, for example diisopropyl azodicarboxylate.

When it is present in the reaction medium, the coupling agent is incorporated into the medium in a proportion of from 0.9 to 5 equivalents and better still in a proportion of from 0.9 to 3 equivalents, for example in a proportion of from 0.9 to 2 molar equivalents relative to the initial amount of compound of the formula (II).

Preferably, it is also recommended to introduce a phosphine into the reaction medium, such as triphenylphosphine. In this case, the molar ratio of triphenylphosphine to the compound of the formula (II) is preferably maintained between 0.9 and 5, for example between 0.9 and 3 and especially between 0.9 and 2.

The reaction temperature generally ranges between −15° C. and +60° C.

According to one advantageous embodiment, the compounds of the formula (I) in which R represents hydrogen can be obtained by saponification of the corresponding compounds of the formula (I) in which R represents a $C_1$-$C_{10}$ alkyl radical.

The saponification can be performed via the action of a base, such as a mineral base chosen from lithium hydroxide, potassium hydroxide, sodium hydroxide, sodium hydrogen carbonate, potassium hydrogen carbonate, sodium carbonate and potassium carbonate. The molar amount of base to be used generally ranges from 1 to 20 equivalents and preferably from 1 to 12 equivalents depending on the strength of the selected base.

The reaction is preferably performed in a solvent of polar protic type and more preferably in a mixture of lower ($C_1$-$C_4$) alkanol and water, such as a mixture of ethanol and water or of methanol and water.

The reaction temperature advantageously ranges between 35° C. and 120° C. and better still between 40° C. and 100° C.

One preferred embodiment of the general preparation process according to the invention follows the reaction scheme below:

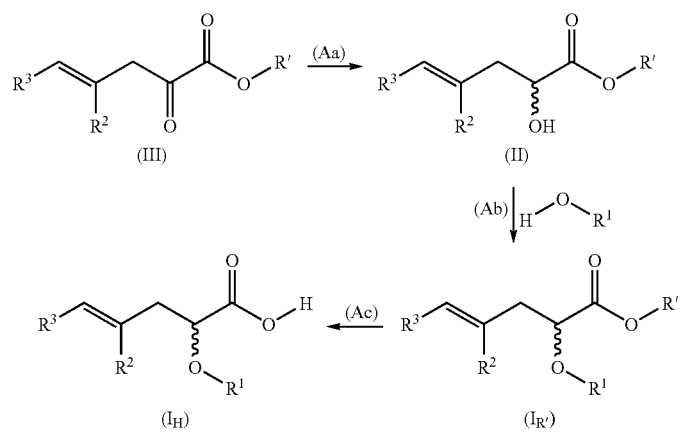

(Aa): NaBH$_4$/ EtOH
(Ab): toluene/ PPh$_3$/ DIAD/ room temp.
(Ac): EtOH/ KOH/ H$_2$O reflux in which reaction scheme $R^1$, $R^2$ and $R^3$ are as defined above for formula (I), R' represents R as defined above, with the exception of hydrogen, the compound ($I_{R'}$) being the compound of the formula (I) in which R represents a $C_1$-$C_{10}$ alkyl radical, as defined above, and the compound ($I_H$) being the compound of the formula (I) in which R represents —H. PPh$_3$ means triphenylphosphine, DIAD means diisopropyl azodicarboxylate, "room temp." means room temperature, EtOH is ethanol and KOH is potassium hydroxide.

In the above reaction scheme, the saponification reaction step (Ac) is optional, i.e. it is performed only in the case where the desired compound of the formula (I) is a carboxylic acid (R=H).

In addition, and according to another embodiment of the process according to the invention, the compounds of the formula ($I_G$), which is a special case of the compounds of the formula (I) in which $R^1$ represents an aryl radical substituted by a radical G as defined above, can be prepared according to the following reaction scheme:

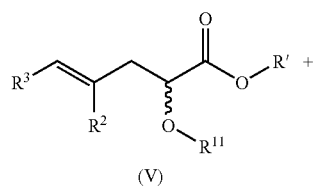

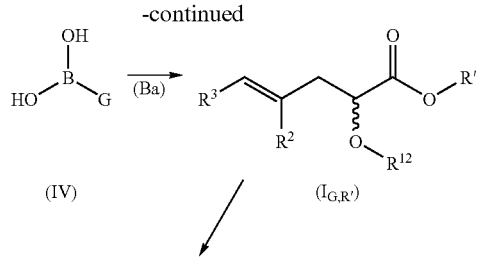

(Ba): CH$_3$OCH$_2$CH$_2$OCH$_3$/ Pd(PPh$_3$)$_4$/ Na$_2$CO$_3$/ H$_2$O
(Bb): EtOH/ KOH/ H$_2$O/ reflux in which reaction scheme:
$R^2$ and $R^3$ are as defined above for formula (I);
R' represents R, as defined above, with the exception of hydrogen;
$R^{11}$ represents $R^1$, as defined above, bearing a group that is reactive with the derivative of the formula (IV) and chosen especially from a bromine or iodine atom and a CF$_3$SO$_3$— radical, bromine and iodine being the preferred reactive groups; and
$R^{12}$ represents $R^{11}$, in which the group that is reactive with the derivative of the formula (IV) has been substituted by the radical G.

As indicated in the above reaction schemes, the saponification step (Bb) is optional. The compounds of the formulae ($I_{G, R'}$) and ($I_{G, H}$) form the set of compounds of the formula ($I_G$), which is a special case of the compounds of the formula (I) in which $R^1$ represents an aryl radical substituted by a radical G.

Thus, the compounds of the formula (I) in which $R^1$ represents aryl substituted by a monocyclic, bicyclic or tricyclic aromatic heterocyclic group G comprising one or more hetero atoms chosen from O, N and S, and optionally substituted by one or more radicals T as defined above, or alternatively in which $R^1$ represents an aryl group optionally substituted by one or more radicals T, can be prepared by reaction of the corresponding compound of the formula (I) in which $R^1$ represents aryl substituted by a halogen atom, such as chlorine, bromine or iodine, with a compound of the formula (VI) defined in the above reaction scheme, in which G represents a monocyclic, bicyclic or tricyclic aromatic heterocyclic group comprising one or more hetero atoms chosen from O, N and S, and optionally substituted by one or more radicals T as defined above when $R^1$, in the final compound, represents aryl substituted by such a heterocyclic group, or alternatively G represents aryl optionally substituted by one or more radicals T when, in the final compound, $R^1$ represents aryl substituted by an aryl group, which is itself optionally substituted by one or more radicals T.

Advantageously, from 1.5 to 5 equivalents and preferably from 1.5 to 3 equivalents of the compound of the formula (V) are incorporated relative to the amount of starting compound present in the reaction medium.

This reaction is preferably performed in a polar aprotic solvent in the presence of a palladium 0 complex and a base.

A linear or cyclic ether, such as those defined above is more particularly suitable as solvent. Dimethoxyethane is preferred.

The base that will be used is any of the mineral bases mentioned above and advantageously sodium carbonate. For example, from 1.5 to 5 equivalents and preferably from 1.5 to 3 equivalents of base, relative to the amount of starting compound, can be introduced into the reaction medium.

The amount of palladium 0 complex used is catalytic. Usually, from 0.001 to 1 equivalent and preferably from 0.01 to 0.1 equivalent of the said complex is used. An example of a palladium 0 complex that can be used is tetrakis(triphenylphosphine)palladium 0.

The reaction temperature advantageously ranges between 50° C. and 120° C. and preferably between 70° C. and 90° C.

This embodiment and the compounds resulting therefrom are illustrated in the Examples section below.

In the processes described above, it should be understood that the operating conditions may vary substantially depending on the various substituents present in the compounds of the formula (I) that it is desired to prepare. Such variations and adaptations are readily available to a person skilled in the art, for example from scientific reviews, the patent literature, Chemical Abstracts, and computer databases, including the Internet. Similarly, the starting materials are either commercially available or are available via syntheses that a person skilled in the art can readily find, for example in the various publications and databases described above.

The optical isomers of the compounds of the formula (I) can be obtained, on the one hand, via standard techniques for separating and/or purifying isomers, known to those skilled in the art, from the racemic mixture of the compound of the formula (I). The optical isomers can also be obtained directly via stereoselective synthesis of an optically active starting compound.

The examples that follow illustrate the present invention without limiting it in any way. In these examples and in the proton nuclear magnetic resonance (300 MHz NMR) data, the following abbreviations have been used: s for singlet, d for doublet, t for triplet, q for quartet, o for octet and m for complex multiplet. The chemical shifts δ are expressed in ppm. "M.p." means "melting point".

EXAMPLES

Example 1

Process for the Preparation of ethyl (R,S)-2-{[4-(2-methyl-1,3-thiazol-4-yl)phenyl]oxy}-5-phenylpent-4-enoate Step a): Ethyl (R,S)-2-hydroxy-5-phenylpent-4-enoate 1.1 g (28 mmol) of sodium borohydride are added over 15 minutes to a suspension of 20.1 g (92 mmol) of ethyl 2-oxo-5-phenylpent-4-enoate (*C. R. Hebd. Séances Acad. Sci.*, (1957), 235, 1548) in 400 ml of pharmaceutical-grade ethanol. Gradual dissolution is observed, accompanied by mild exothermicity. The mixture is then stirred for 45 minutes at room temperature, after which the solvent is evaporated off under vacuum. The residue is taken up in 300 ml of water, extracted with dichloromethane and dried over sodium sulfate, and the solvent is evaporated off under vacuum. 17.1 g (84%) of an amber-coloured oil are obtained.

$^1$H NMR (CDCl$_3$, 300 MHz): 1.55 (3H, t, J=7 Hz); 2.78-3.12 (3H, m); 4.40-4.57 (3H, m); 6.38-6.46 (1H, m); 6.72 (1H, d, J=16 Hz); 7.42-7.59 (5H, m).

Step b): Ethyl (R,S)-2-{[4-(2-methyl-1,3-thiazol-4-yl)phenyl]oxy}-5-phenylpent-4-enoate 2.6 g (13.5 mmol) of 4-(2-methyl-1,3-thiazol-4-yl)phenol and 3.3 g (15 mmol) of ethyl (R,S)-2-hydroxy-5-phenylpent-4-enoate obtained in step a) are added to a stirred solution, under nitrogen, of 3.85 g (14.7 mmol) of triphenylphosphine in 70 ml of toluene. The solution obtained is heated to 55° C. and 2.9 g (14.3 mmol) of diisopropyl azodicarboxylate (DIAD) dissolved in 10 ml of toluene are added dropwise over 45 minutes. The reaction medium is then stirred at this same temperature for one hour, it is cooled to room temperature and stirring is then continued overnight.

The resulting mixture is cooled to 0° C. for one hour and the precipitate formed is then filtered off by suction and discarded. The filtrate is evaporated to dryness under vacuum.

The residual amber-coloured oil is purified by two successive flash chromatographies on silica, i.e.:

elution with 85/15 heptane/ethyl acetate, and then
63/7/30 heptane/ethyl acetate/trichloromethane.

1.83 g of a yellow oil that crystallizes are obtained.
Yield=34.5%

$^1$H NMR (CDCl$_3$, 300 MHz): 1.15 (3H, t, J=7 Hz); 2.68 (3H, s); 2.81 (2H, t, J=7 Hz); 4.14 (2H, q, J=7 Hz); 4.70 (1H, t, J=6 Hz); 6.17-6.25 (1H, m); 6.47 (1H, d, J=16 Hz); 6.87 (2H, d, J=7 Hz); 7.14-7.30 (6H, m); 7.71 (2H, d, J=6 Hz).

Example 2

Process for the Preparation of (R,S)-2-{[4-(2-methyl-1,3-thiazol-4-yl)phenyl]oxy})-5-phenylpent-4-enoic acid 1.8 g (28 mmol) of 85% potassium hydroxide pellets are added to a stirred solution of 2.2 g (5.6 mmol) of the ester obtained in Example 1, in 100 ml of pharmaceutical-grade ethanol. The mixture is refluxed for 30 minutes. 10 ml of water are added to the solution obtained, and refluxing is then continued for 4 hours 30 minutes. The resulting mixture is cooled to room temperature and evaporated to dryness under vacuum. The residual gum is dissolved in 40 ml of water. The aqueous phase is washed with dichloromethane and then acidified with 6N hydrochloric acid. The precipitate formed is filtered off by suction and washed with water. After drying under vacuum at 80° C., 1.45 g of a beige-coloured solid are obtained. M.p.=187-188° C.

Yield=72%

$^1$H NMR (CDCl$_3$, 300 MHz): 2.68 (3H, s); 2.73-2.98 (2H, m); 4.82-5.00 (1H, m); 6.21-6.24 (2H, m) 6.87-7.01 (2H, m); 7.12-7.46 (5H, m); 7.66-7.95 (3H, m); 13.15 (1H, broad s).

Example 3

Process for the Preparation of ethyl (R,S)-2-[(4-bromophenyl)oxy]-5-phenylpent-4-enoate 1.5 g (9 mmol) of 4-bromophenol and 2.2 g (10 mmol) of ethyl (R,S)-2-hydroxy-5-phenylpent-4-enoate are added to a stirred solution, under nitrogen, of 2.5 g (9.8 mmol) of triphenylphosphine (Ph$_3$P) in 50 ml of toluene. The solution obtained is heated to 55° C., and 1.9 g (9.5 mmol) of diisopropyl azodicarboxylate (DIAD) dissolved in 10 ml of toluene are added dropwise over 45 minutes. The reaction medium is then stirred at this temperature for one hour, it is cooled to room temperature and stirring is then continued overnight.

The resulting mixture is cooled to 0° C. for one hour and the precipitate formed is filtered off by suction and discarded. The filtrate is evaporated to dryness under vacuum. The residue is purified by flash chromatography on silica, eluting with 95/5 heptane/ethyl acetate.

2 g of a yellow oil are obtained.

Yield=59%

$^1$H NMR (CDCl$_3$, 300 MHz): 1.15 (3H, t, J=7 Hz); 2.78 (2H, t, J=6 Hz); 4.14 (2H, q, J=7 Hz); 4.61 (1H, t, J=6 Hz); 6.13-6.21 (1H, m); 6.46 (1H, d, J=16 Hz); 6.73 (2H, m); 7.14-7.31 (7H, m).

Example 4

Process for the Preparation of (R,S)-2-[(4-bromophenyl)oxy]-5-phenylpent-4-enoic acid The ester of Example 3 is used in a saponification reaction, according to the procedure given in Example 2, to give the expected carboxylic acid.

$^1$H NMR (CDCl$_3$, 300 MHz): 2.77-3.01 (2H, m); 4.65-4.80 (1H, m); 6.12-6.35 (1H, m); 6.45-6.60 (1H, m); 6.68-6.87 (2H, m); 7.13-7.53 (7H, m).

Example 5

Process for the Preparation of ethyl (R,S)-2-{[4-(benzo[b]thiophen-2-yl)phenyl]oxy}-5-phenylpent-4-enoate 245 mg (0.21 mmol) of tetrakis(triphenylphosphine)palladium and 1.9 g (10.6 mmol) of thianaphthene-2-boronic acid are added to a stirred solution, under nitrogen, of 2 g (5.3 mmol) of the bromo derivative obtained in Example 3, in 70 ml of dimethoxyethane.

6.5 ml (13 mmol) of aqueous 2N sodium carbonate solution are then added dropwise.

The reaction medium is then refluxed for two hours, and is then stirred overnight at room temperature.

The resulting mixture is poured into 300 ml of water and extracted with twice 100 ml of ethyl ether. The organic phase is dried over sodium sulfate and then evaporated under vacuum.

The residue is purified by flash chromatography on silica, eluting with 95/5 heptane/ethyl acetate.

0.9 g of a beige-coloured solid is obtained.

Yield=40%

$^1$H NMR (CDCl$_3$, 300 MHz): 1.18 (3H, t, J=7 Hz); 2.83 (2H, t, J=6 Hz); 4.17 (2H, q, J=7 Hz); 4.71, (1H, t, J=6 Hz); 6.17-6.27 (1H, m); 6.49 (1H, d, J=16 Hz); 6.89 (2H, d, J=9 Hz); 7.13-7.36 (8H, m); 7.56 (2H, d, J=9 Hz); 7.67 (1H, d, J=8 Hz) ; 7.73 (1H, d, J=8 Hz).

Example 6

Process for the Preparation of (R,S)-2-{[4-(benzo[b]thiophen-2-yl)phenyl]oxy}-5-phenylpent-4-enoic acid 640 mg (10.5 mmol) of 85% potassium hydroxide pellets are added to a stirred solution of 0.9 g (2.1 mmol) of the ester obtained above, in 50 ml of pharmaceutical-grade ethanol. The mixture is refluxed for 30 minutes.

3.5 ml of water are added to the solution obtained, and refluxing is continued for 3 hours 30 minutes.

The resulting mixture is cooled to room temperature and evaporated to dryness under vacuum. 50 ml of water are added to the solid obtained, and the suspension is acidified with 6N hydrochloric acid, with stirring. The mixture is stirred for 30 minutes and the insoluble matter is then extracted with ethyl acetate. The organic phase is dried over sodium sulfate and evaporated to dryness under vacuum.

0.74 g of a solid is obtained. M.p.=170° C.

Yield=88%

$^1$H NMR (DMSO-d6, 300 MHz): 2.66-2.96 (2H, m); 4.84-5.08 (1H, m); 6.18-6.69 (2H, m); 6.89-7.52 (9H, m); 7.56-8.08 (5H, m); 13.21 (1H, broad s).

The compounds of Examples 7 to 9 below are prepared according to procedures similar to those described above.

| Example | R | R$^1$ | R$^2$ | R$^3$ | $^1$H NMR(300MHz) analysis |
|---|---|---|---|---|---|
| 7 | —H | ![4-(5-chlorothiophen-2-yl)phenyl group] | —H | ![phenyl group] | (CDCl$_3$): 2.90(2H, m); 4.80 (1H, m); 6.11-6.39(1H, m); 6.43-6.69(1H, m); 6.69-7.05 (4H, m); 7.10-7.60(7H, m). |

-continued

| Example | R | R$^1$ | R$^2$ | R$^3$ | $^1$H NMR(300MHz) analysis |
|---|---|---|---|---|---|
| 8 | —Et | 4-(CF$_3$)phenyl-CH$_2$– type structure (tolyl with CF$_3$) | —H | —H | (CDCl$_3$): 1.24(3H, t, J=7.2Hz); 2.72(2H, m); 4.22 (2H, q, J=7.2Hz); 4.71, (1H, m); 5.05-5.29(2H, m); 5.88 (1H, m); 6.94(2H, d, J=8.7Hz); 7.53(2H, d, J=8.7Hz). |
| 9 | —H | (tolyl with CF$_3$) | —H | —H | (CDCl$_3$): 2.76(2H, m); 4.77 (1H, m); 5.09-5.34(2H, m); 5.89(1H, m); 6.96(2H, d, J=9.0Hz); 7.63(2H, d, J=9.0Hz). |

BIOLOGICAL EXPERIMENTAL SECTION

Biological Activity Tests

The activity of the compounds of the invention leading to a hypolipidaemiant and hypoglycaemiant effect was demonstrated in vitro and in vivo by performing the following tests:

The measurement of the PPAR activation was performed according to a lo technique described by Lehmann et al. (1995, *J. Biol. Chem.*, 270, 12953-12956).

CV-1 cells (monkey kidney cells) are co-transfected with an expression vector for the chimeric proteins PPARα-Gal4 or PPARγ-Gal4 and with a "reporter" plasmid that allows the expression of the luciferase gene placed under the control of a promoter comprising Gal4 response elements.

The cells are plated into 96-well microplates and co-transfected using a commercial reagent with the reporter plasmid (pG5-tk-pGL3) and the expression vector for the chimeric protein (PPARα-Gal4 or PPARγ-Gal4). After incubating for 4 hours, whole culture medium (comprising 10% foetal calf serum) is added to the wells. After 24 hours, the medium is removed and replaced with whole medium comprising the test products (50 μM final). The products are left in contact with the cells for 18 hours. The cells are then lysed and the luciferase activity is measured using a luminometer. A PPAR activation factor can then be calculated by means of activation of the expression of the reporter gene induced by the product (relative to the control cells that have not received any product).

By way of example, the compound of Example 6 at a concentration of 50 μM, activates the chimeric protein PPARα-Gal-4 by a factor of 7, and the chimeric protein PPARγ-Gal4 by a factor of 21. In the absence of the binding domain for the PPAR α or γ ligand (vector expressing Gal4 alone), the luciferase activity measured in the presence of this product is zero.

EXAMPLE

Compound of Example 6

The antidiabetic and hypolipidaemiant activity of the compounds was determined orally on db/db mice.

Nine-week-old db/db mice are treated orally for 15 days with the compound of Example 6 (100 mg/kg/day). Each group studied comprises seven animals. After treatment for 15 days, retro-orbital samples are taken under mild anaesthesia and after fasting for four hours.

The following parameters were measured:

Assay of the glycaemia (glucose oxidase) and of the lipid parameters on the sera at D15 (COBAS): triglycerides, total cholesterol (CHOL), HDL cholesterol (HDL-C) and free fatty acids (FFA) (BioMérieux and Waco Chemicals assay kit).

The results obtained are given in the table below. The measurements reported represent mean values±standard error.

|  | Control | Example 6 | % var. |
|---|---|---|---|
| Glycaemia Mm | 30.02 ± 4.42 | 14.93 ± 4.29 | −50% (**) |
| Triglycerides mM | 2.14 ± 0.47 | 1.47 ± 0.59 | −31% (*) |
| HDL-C Mm | 3.07 ± 0.26 | 2.31 ± 0.20 | −25% (**) |
| CHOL mM | 3.75 ± 0.37 | 2.98 ± 0.25 | −20% (**) |
| FFA mM | 0.86 ± 0.08 | 0.78 ± 0.18 | −10% (ns) |

% var: percentage of variation versus control.
Mann-Whitney test:
(*): p < 0.05 versus control
(**): p < 0.01 versus control
(ns): not significant

The invention claimed is:
1. Compound of the formula (I):

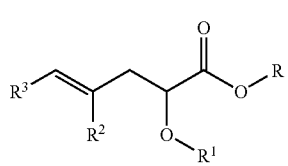

(I)

in which:
R$^1$ represents a (C$_6$-C$_{18}$)aryl radical substituted by and/or fused to a saturated or unsaturated 5- to 8-membered monocyclic or polycyclic nucleus optionally containing one or more hetero atoms chosen from O, N and S, the said nucleus itself being optionally substituted;
R$^2$ and R$^3$, which may be identical or different, are chosen, independently of each other, from a hydrogen atom and a (C$_6$-C$_{18}$)aryl radical; and
R is chosen from a hydrogen atom and a C$_1$-C$_{10}$ alkyl radical;
the geometrical and optical isomers thereof, and also the pharmaceutically acceptable addition salts thereof with acids or bases, it being understood that the compound in which $R^2$=H, $R^3$=H, R=H or ethyl and $R^1$=(2-chloro-4-trifluoromethylphenoxy)phenyl is excluded from protection.

2. Compound according to claim 1, in which $R^1$ represents substituted $(C_6$-$C_{10})$aryl;

$R^2$ and $R^3$, which may be identical or different, are chosen, independently of each other, from a hydrogen atom and a $(C_6$-$C_{10})$aryl radical; and R is chosen from a hydrogen atom and a $C_1$-$C_{10}$ radical.

3. Compound according to claim 1, characterized in that when $R^1$ represents a substituted $(C_6$-$C_{10})$aryl radical, the aryl nucleus is substituted by one or more of the following radicals:

trifluoromethyl; a halogen atom; a monocyclic, bicyclic or tricyclic aromatic heterocycic radical comprising one or more hetero atoms chosen from O, N and S; and optionally substituted by one or more radicals T as defined below; a group Het-CO—, in which Het represents an aromatic heterocyclic radical optionally substituted by one or more radicals T; a $C_1$-$C_6$ alkylenediyl chain; a $C_1$-$C_6$ alkylenedioxy chain; nitro; cyano; $(C_1$-$C_{10})$alkyl; $(C_1$-$C_{10})$alkylcarbonyl; $(C_1$-$C_{10})$alkoxycarbonyl-A-, in which A represents $(C_1$-$C_6)$alkylene, $(C_2$-$C_6)$alkenylene or a bond; $(C_3$-$C_{10})$cycloalkyl; trifluoromethoxy; di$(C_1$-$C_{10})$alkylamino; $(C_1$-$C_{10})$alkoxy$(C_1$-$C_{10})$alkyl; $(C_1$-$C_{10})$alkoxy; $(C_6$-$C_{18})$aryl optionally substituted by one or more radicals T; $(C_6$-$C_{18})$aryl$(C_1$-$C_{10})$alkoxy-$(CO)_n$—, in which n is 0 or 1 and aryl is optionally substituted by one or more radicals T; $(C_6$-$C_{18})$aryloxy $(CO)_n$—, in which n is 0 or 1 and in which aryl is optionally substituted by one or more radicals T; $(C_6$-$C_{18})$arylthio, in which aryl is optionally substituted by one or more radicals T; $(C_6$-$C_{18})$aryloxy$(C_1$-$C_{10})$alkyl $(CO)_n$—, in which n is 0 or 1 and in which aryl is optionally substituted by one or more radicals T; a saturated or unsaturated, monocyclic 5- to 8-membered heterocycle comprising one or more hetero atoms chosen from O, N and S, optionally substituted by one or more radicals T; $(C_6$-$C_{18})$-arylcarbonyl optionally substituted by one or more radicals T; $(C_6$-$C_{18})$arylcarbonyl-B—$(CO)_n$—, in which n is 0 or 1; B represents $(C_1$-$C_6)$ alkylene or $(C_2$-$C_6)$alkenylene and aryl is optionally substituted by one or more radicals T; $(C_6$-$C_{18})$aryl-C—$(CO)_n$—, in which n is 0 or 1, C represents $(C_1$-$C_6)$ alkylene or $(C_2$-$C_6)$alkenylene and aryl is optionally substituted by one or more radicals T; $(C_6$-$C_{18})$aryl fused to a saturated or unsaturated heterocycle optionally substituted by one or more radicals T; $(C_2$-$C_{10})$ alkynyl; T is chosen from a halogen atom; $(C_6$-$C_{18})$aryl; $(C_1$-$C_6)$alkyl; $(C_1$-$C_6)$alkoxy; nitro; carboxyl; $(C_1$-$C_6)$ alkoxycarboxyl; and T may represent oxo in the case where it substitutes a saturated or unsaturated heterocycle; or T represents $(C_1$-$C_6)$alkoxycarbonyl$(C_1$-$C_6)$ alkyl; or $(C_1$-$C_6)$alkylcarbonyl$((C_1$-$C_6)$alkyl)_n$—, in which n is 0 or 1.

4. Compound according to claim 1, in which $R^2$ a hydrogen atom.

5. Compound according to claim 1, in which $R^3$ is chosen from a hydrogen atom and an unsubstituted $(C_6$-$C_{10})$aryl group.

6. Compound according to claim 1, characterized in that $R^3$ represents unsubstituted phenyl.

7. Compound according to claim 1 of the formula I, chosen from:

(R,S)-2-{[4-(5-chlorothien-2-yl)phenyl)oxy}-5-phenylpent-4-enoic acid;

(R,S)-2-{[(4-benzo[b]thiophen-2-yl)phenyl]oxy}-5-phenylpent-4-enoic acid; and (R,S)-2-{[4-(2-methyl-1,3-thiazol-4-yl)phenyl]oxy}-5-phenylpent-4-enoic acid.

8. Pharmaceutical composition comprising a pharmaceutically effective amount of at least one compound of the formula (I) according to claim 1, and at least one pharmaceutically acceptable vehicle.

9. A process for the preparation of a compound of the formula (I) according to claim 1, comprising reacting a compound of formula (III)

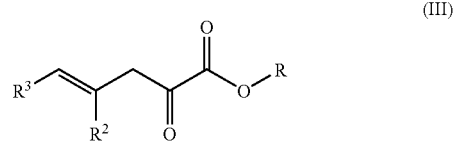

to produce a compound of formula II

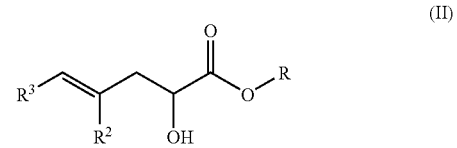

and reacting formula II with a compound of formula $R^1$—OH in which reactions $R^1$, $R^2$, $R^3$ and R are as defined in claim 1.

10. A process for the production of a compound of formula I according to claim 1, comprising reacting a compound of formula $R^1$—OH with a compound of formula II

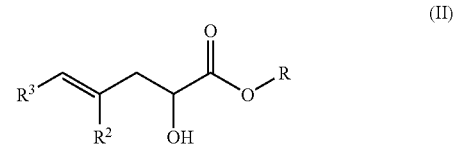

which has been prepared from a compound of formula III

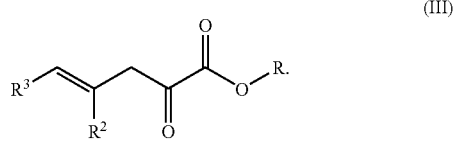

11. A process according to claim 9 for the preparation of a compound of the formula (I), comprising:

(Aa) reacting a compound of formula III

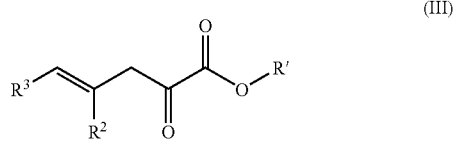

to produce a compound of formula II

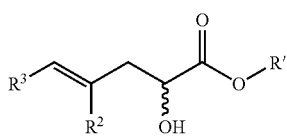
(II)

(Ab) reacting formula II with R¹—OH to produce a compound of formula I R'

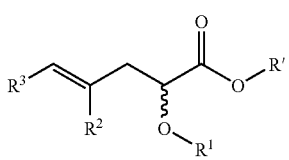
(I$_{R'}$)

and optionally (Ac) reacting I$_{R'}$ to produce I$_{H'}$

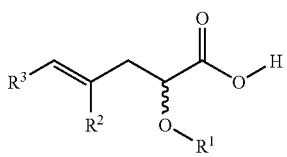
(I$_H$)

in which reactions R¹, R² and R³ are as defined for formula (I), R' represents R as defined above, with the exception of hydrogen, the compound (I$_{R'}$) being the compound of the formula (I) in which R represents a $C_1$-$C_{10}$ alkyl radical, as defined above, wherein (Ab) is performed in an aromatic solvent or in a polar aprotic solvent, in the presence of a coupling agent and a phosphine, at a temperature of –15° C. to +60° C.; and (Ac) is an optional saponification reaction.

12. A process according to claim 11, wherein (Aa) is conducted in NaBH$_4$/ETOH, (Ab) is conducted in toluene/PPh$_3$/diisopropyl azodicarboxylate at room temperature, and optional (Ac) is conducted in ETOH/KOH/H$_2$O at reflux.

13. A process for the preparation of a compound of formula I according to claim 1, in which R¹ represents an aryl radical substituted by a radical G, comprising (Ba) reacting, in a polar aprotic solvent in the presence of a palladium 0 complex and a base, a compound of formula V

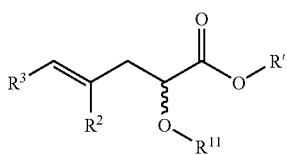
(V)

with a compound of formula IV

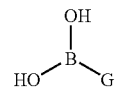
(IV)

to produce a compound of formula I$_{G'R'}$

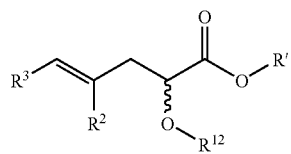
(I$_{G,R'}$)

and (Bb) optionally saponifying I$_{G'R'}$ to produce

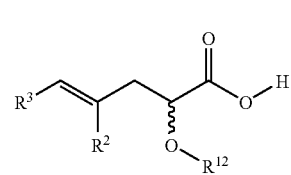
(I$_{G,H}$)

wherein:
R² and R³ are as defined in claim 1 for formula (I);
R' represents R, as defined above, with the exception of hydrogen;
R¹¹ represents R¹, as defined above, bearing a group that is reactive with formula (IV) and
R¹² represents R¹¹, in which the group that is reactive with the derivative of the formula (IV) has been substituted by the radical G,
G is trifluoromethyl; a halogen atom; a monocyclic, bicyclic or tricyclic aromatic heterocyclic radical comprising one or more hetero atoms chosen from O, N and S; and optionally substituted by one or more radicals T as defined below; a group Het-CO—, in which Het represents an aromatic heterocyclic radical as defined above optionally substituted by one or more radicals T; a $C_1$-$C_6$ alkylenediyl chain; a alkylenedioxy chain; nitro; cyano; ($C_1$-$C_{10}$)alkyl; ($C_1$-$C_{10}$)alkylcarbonyl; ($C_1$-$C_{10}$)-alkoxycarbonyl-A-, in which A represents ($C_1$-$C_6$)alkylene, ($C_2$-$C_6$)alkenylene or a bond; ($C_3$-$C_{10}$)cycloalkyl; trifluoromethoxy; di($C_1$-$C_{10}$)alkylamino; ($C_1$-$C_{10}$) alkoxy($C_1$-$C_{10}$)alkyl; ($C_1$-$C_{10}$)alkoxy; ($C_6$-$C_{18}$)aryl optionally substituted by one or more radicals T; ($C_6$-$C_{18}$)alyl($C_1$-$C_{10}$)alkoxy-(CO)$_n$—, in which n is 0 or 1 and aryl is optionally substituted by one or more radicals T; ($C_6$-$C_{18}$)aryloxy(CO)$_n$—, in which n is 0 or 1 and in which aryl is optionally substituted by one or more radicals T; ($C_6$-$C_{18}$)arylthio, in which aryl is optionally substituted by one or more radicals T; ($C_6$-$C_{18}$)aryloxy($C_1$-$C_{10}$)alkyl (CO)$_n$—, in which n is 0 or 1 and in which aryl is optionally substituted by one or more radicals T; a saturated or unsaturated, monocyclic 5- to 8-membered heterocycle comprising one or more hetero atoms chosen from O, N and S, optionally substituted by one or more radicals T; $(C_6-C_{18})$arylcarbonyl optionally substituted by one or more radicals T; $(C_6-C_{18})$alylcarbonyl-B—$(CO)_n$—, in which n is 0 or 1; B represents $(C_1-C_6)$alkylene or $(C_2-C_6)$alkenylene and aryl is optionally substituted by one or more radicals T; $(C_6-C_{18})$aryl-C—$(CO)_n$—, in which n is 0 or 1, C represents $(C_1-C_6)$alkylene or $(C_2-C_6)$alkenylene and aryl is optionally substituted by one or more radicals T; or $(C_6-C_{18})$aryl fused to a saturated or unsaturated heterocycle as defined above, optionally substituted by one or more radicals T; $(C_2-C_{10})$alkynyl;

T is chosen from a halogen atom; $(C_6-C_{18})$aryl; $(C_1-C_6)$alkyl; $(C_1-C_6)$alkoxy; nitro; carboxyl; $(C_1-C_6)$alkoxycarboxyl; and T may represent oxo in the case where it substitutes a saturated or unsaturated heterocycle; or T represents $(C_1-C_6)$alkoxycarbonyl$(C_1-C_6)$alkyl; or $(C_1-C_6)$alkylcarbonyl$((C_1-C_6)$alkyl$)_n$-, in which n is 0 or 1.

14. A process according to claim 13, wherein in $R^{11}$ the group reactive with formula IV is Br, I or $CF_3SO_3$.

* * * * *

UNITED STATES PATENT AND TRADEMARK OFFICE
CERTIFICATE OF CORRECTION

PATENT NO. : 7,465,752 B2
APPLICATION NO. : 11/568598
DATED : December 16, 2008
INVENTOR(S) : Jean Jacques Zeiller Page 1 of 1

It is certified that error appears in the above-identified patent and that said Letters Patent is hereby corrected as shown below:

On the title page, item [75] Inventors: line 1, reads "Lyons" should read -- Lyon --

On the title page, Inventors: line 6, reads "Lyons" should read -- Lyon --

On the title page, Inventors: line 8, reads "Lyons" should read -- Lyon --

Column 17, line 15, reads "heterocycic" should read -- heterocyclic --

Column 20, line 50, reads "a alkylenedioxy" should read -- a $C_1$-$C_6$ alkylenedioxy --

Column 20, line 57, reads ". . .alyl. . ." should read -- . . .aryl. . . --

Column 21, line 2, reads ". . .alyl. . ." should read -- . . .aryl. . . --

Signed and Sealed this

Seventeenth Day of March, 2009

JOHN DOLL
*Acting Director of the United States Patent and Trademark Office*